United States Patent [19]

Ranani

[11] Patent Number: 4,703,964

[45] Date of Patent: Nov. 3, 1987

[54] TINTED CONTACT LENS FITTER

[76] Inventor: Ami C. Ranani, Fenwood Rd., Mahopac, N.Y. 10541

[21] Appl. No.: 879,372

[22] Filed: Jun. 27, 1986

[51] Int. Cl.⁴ .............................................. G02B 7/02
[52] U.S. Cl. .................................... 294/1.1; 294/1.2; 350/256; 351/229
[58] Field of Search ................ 294/1.1, 1.2, 16, 27.1, 294/28, 118; 51/216 LP; 206/5.1; 350/145, 146, 245–247, 254, 256; 351/227, 229, 230, 231, 235, 245, 247

[56] References Cited

U.S. PATENT DOCUMENTS

| 466,597 | 1/1892 | Borsch | 351/229 |
| 1,086,802 | 2/1914 | Beebe | 350/146 |
| 1,348,092 | 7/1920 | Day | 351/227 |
| 1,384,252 | 7/1921 | Giddens | 351/235 |
| 1,962,800 | 6/1934 | Aspenleiter | 351/229 |
| 2,872,843 | 2/1959 | Kono | 351/230 |
| 3,536,082 | 10/1970 | Kolbeck | 206/5.1 X |
| 4,215,890 | 8/1980 | Savage | 350/256 X |
| 4,326,742 | 4/1982 | Ingram | 294/1.2 |
| 4,415,076 | 11/1983 | Campbell | 206/5.1 |

Primary Examiner—Johnny D. Cherry
Attorney, Agent, or Firm—S. C. Yuter

[57] ABSTRACT

Tinted contact lens fitter having a scissors type support to vary the spacing between pairs of tinted contact lenses mounted in rotatable discs, or in plug-in lens holders, or directly in openings in the support, so that the centers of the tinted contact lenses can be aligned with the centers of a patient's pupils in order for the patient to view in a mirror the combined color of the tinted contact lenses and the color of the patient's irises.

16 Claims, 11 Drawing Figures

TINTED CONTACT LENS FITTER

BACKGROUND OF THE INVENTION

This invention pertains to opthalmic apparatus and, more particularly, to apparatus for fitting tinted contact lens to patients.

DESCRIPTION OF THE RELATED ART

Presently, persons fitting tinted contact lens have to repeatedly try different tinted lens by actually inserting, or having the patient insert, each pair into contact with the patient's eye balls so that the patient can see the color which results from the combined tint of the contact lens and the patient's natural iris color. And often, previously tried tinted contact lens have to be retried in order for the patient to make a final decision as to which tint to order from the many colors which are offered.

Presently available tinted contact lenses are tinted soft contact, hard contact and gas permeable contact lenses. Applicant does not know of any devices to aid in fitting such tinted contact lenses. The closes prior art disclosed by a preliminary examination search are opthalmic lens holders and refracting devices for fitting regular lenses.

BRIEF SUMMARY OF THE INVENTION

Accordingly, the principal object of the invention is to provide apparatus for fitting tinted contact lenses of various types.

A general object of the invention is to substantially reduce the amount of time required to fit tinted contact lenses, and thus reduce the fitting cost.

A more specific object of the invention is to provide apparatus for fitting tinted contact lenses which is relatively simple to construct and easy to use.

These objects of the invention are achieved, in accordance with the invention, by a tinted contact lens fitter comprising means for supporting a pair of tinted contact lenses in lens holders adjacent to and in spaced alignment with the pupils of a patient's eyes so the patient can see the resulting combination color of the tint and the natural color of the patient's iris.

In the preferred embodiment of the invention, a scissors-type supporting means is used to vary the spacing between a pair of tinted contact lenses in lens holders which plug into openings in the scissors-type supporting means, so that different tinted contact lens can easily be tried.

In another embodiment of the invention, rotatable discs, each including a plurality of mounted tinted contact lenses, are interchangeably attached to the supporting means so that different colors may be tried by rotating the discs and changing the discs.

An advantage of the invention is that one or more of the supporting means may be sold in a kit including many pair of plug-in lens holders, with each pair containing differently tinted contact lenses permanently mounted in the lens holders.

Other objects, features and advantages of the invention will be obvious from the following Detailed Description of Embodiments of the Invention taken together with the accompanying two sheets of drawing in which:

FIG. (FIG. 1) is a perspective front elevational view of the preferred embodiment of the invention showing a tinted contact lens fitter having a scissors support to control the spacing between two plug-in tinted contact lens holders.

DETAILED DESCRIPTION OF THE EMBODIMENTS

Figure 1:
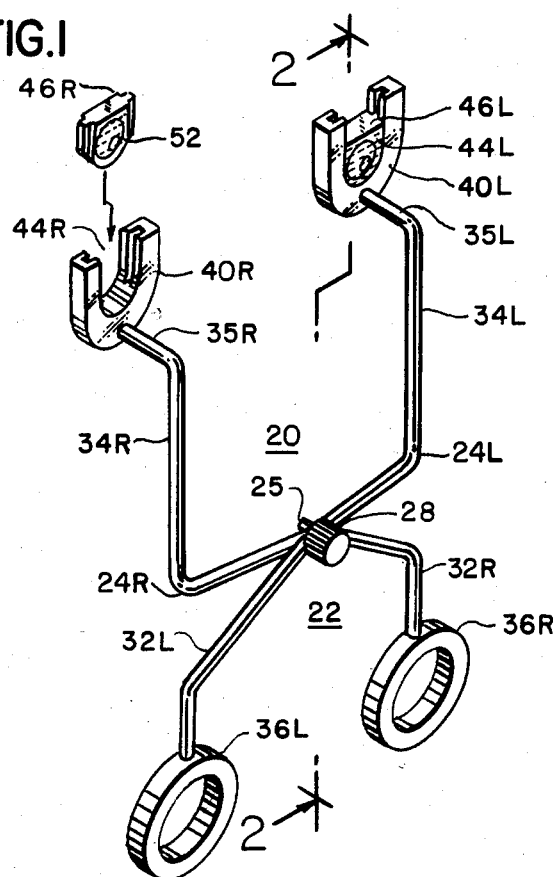
Figure 2:
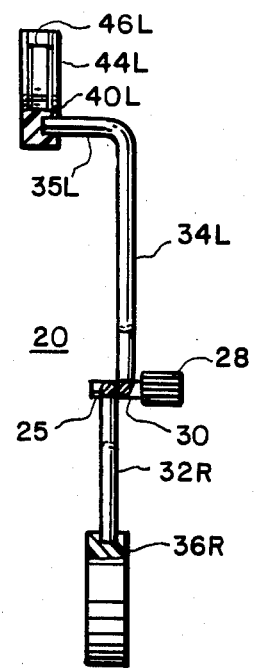
FIG. 2 is a sectional side view of the tinted contact lens fitter shown in FIG. 1 showing a soft tinted contact lens immersed in a saline solution.

Referring to FIGS. 1-4, a tinted contact lens fitter 20 for fitting soft tinted contact lens is shown in accordance with the preferred embodiment of the invention. Tinted contact lens fitter 20 comprises a scissors support assembly 22 having left and right levers 24L and 24R hingedly connected at hinge 28. Hinge 28 consists of knob 28, an attached shaft 30 passing through a hole in each of the levers 24L and 24R and a nut 25 at the end of shaft 30. The tinted contact lens fitter 20 is set into a fixed position by tightening the knob 28 after the angle between levers 24L and 24R is set to a desired angle.

Each of the levers 24 comprises a handle 32L or 32R on one side of the hinge 28 and a shank 34R or 34L on the other side of the hinge 28. At the end of handle 32L is a ring 36L, and a matching ring 36R is at the end of handle 32R.

A lens receptacle 40R is fixed to the end of shank 34R via a 90 degree bent elbow portion 35R, and a lens receptacle 40L is fixed to the end of shank 34L via a 90 degree bent elbow portion 35L.

Each of the lens receptacles 40L and 40R is a clear plastic U having a U-shaped opening 44L or 44R adapted to receive a correspondingly shaped lens holder 46L or 46R.

Figure 3:
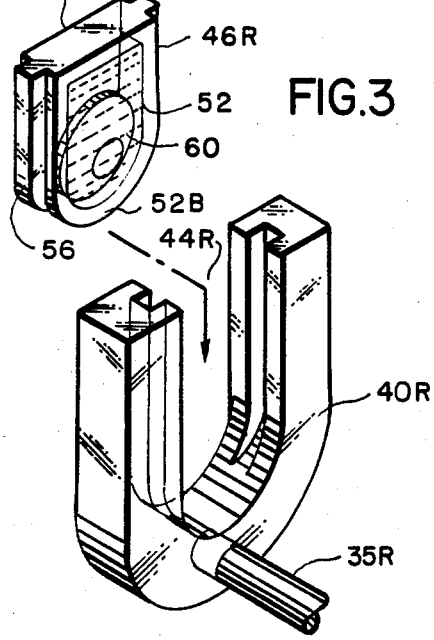
FIG. 3 is a more detailed and perspective view of a lens receptacle and plug-in lens holder of the tinted contact lens fitter of FIG. 1.
Figure 4:
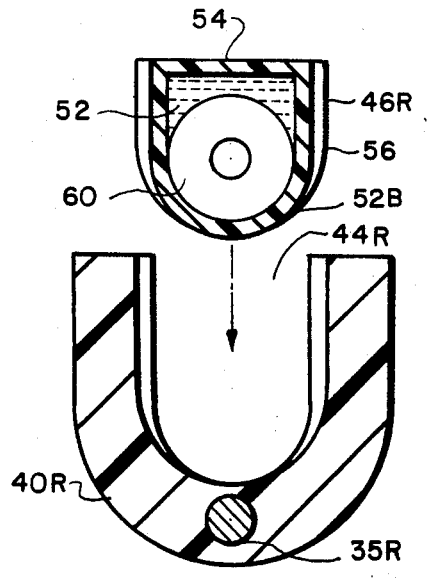
FIG. 4 is a detailed front elevational sectional view of the lens receptacle and plug-in lens holder of FIG. 3 showing the flap for sealing a contact lens immersed in the saline solution in the well of the lens holder.

The lens holder 46R is shown in greater detail in FIGS. 3 and 4. Lens holder 46R comprises a clear plastic body having a well 52 covered by a closure 54. The body has, on each side, an extended guide rail 56 which slides into correspondingly shaped grooves at each side of the opening 44R in lens receptacle 40R. Thus, lens holder 46R is adapted to plug into lens receptacle 40R.

In preparation for using tinted contact lens fitter 20, a saline solution is poured into well 52 to adjacent the top of the well. Then a soft tinted contact lens 60 is carefully dropped into the saline solution and sinks to the arcuate bottom 52B of the well 52. The radius of the arcuate bottom 52B is substantially the same as the radius of the tinted contact lens 60 so that the lens 60 rests in contact with the arcuate bottom 52B when the lens holder 46 is held in a vertical position. Then the closure 54 is inserted at the top of the well 52, sealing the well 52 by a sealing means (not shown), thus sealing the saline solution and the tinted contact lens 60 within the well 52.

Pairs of lens holders 46, each pair containing a pair of soft contact lens 60 of the same tint, are prepared for each available color.

Then a matched pair of lens holders 46 is plugged into the openings 44 of lens receptacles 40 by sliding their guide rails 56 into the grooves 58.

Figure 11:
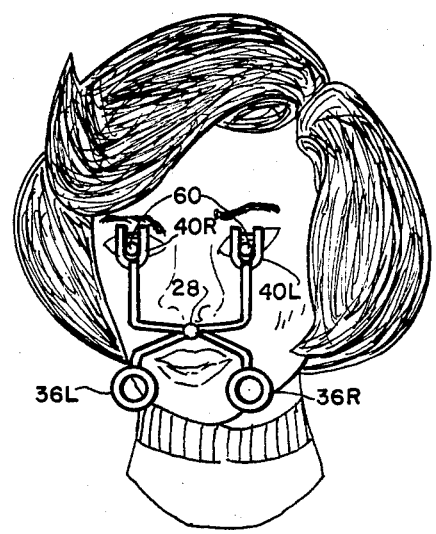
FIG. 11 shows how the preferred embodiment of the tinted contact lens fitter of FIG. 1 is used by a patient to align the center of each of the tinted contact lens with the center of each pupil so that the combined color of the tinted lens and the natural color of the patient's iris can be viewed in a mirror (not shown).

FIG. 11 (sheet 2) shows how the tinted contact lens fitter 20 is used by a patient, with the help of the opthamologist or optometrist fitting a pair of tinted contact lens. With a thumb and forefinger inserted into rings 36, the spacing between lens receptacles 40R and 40L is adjusted and knob 28 tightened so that the lateral distance between the centers of the soft contact lens 60 in the lens receptacles 40R and 40L is the same as the lateral distance between the centers of the pupils of the patient. That permits the center of each tinted contact lens 60 to be aligned with the center of each pupil so that each contact lens 60 is in alignment with the adjacent iris. Then the patient looks into a mirror (not shown) to see the color resulting from combining the tint of the contact lenses 60 with the natural color of the patient's irises.

Naturally, a patient wants to try different tints to obtain the desired color when a pair of soft contact lens with that same tint is worn by the patient. All the fitter need do is to plug into the lens receptacle 40 different pairs of lens holders 46 containing tinted contact lenses of different tints, and the patient then looks at the resulting colors and makes a decision as to which tint to order.

It should be noted that many older patients require a correction in order to see the resulting colors in a mirror. For such patients, the tinted contact lenses 60 can include a necessary correction; for example, +2 diopters.

Figure 5:
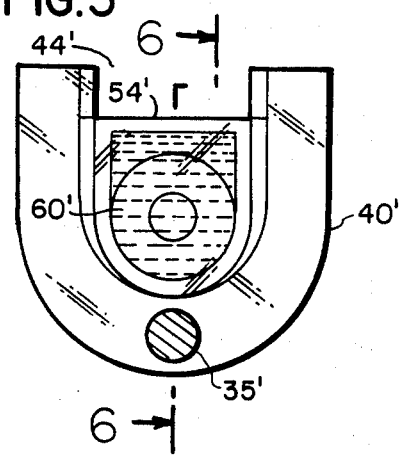
FIG. 5 (on the second sheet) is a front elevational view, partly cutaway, of an alternate embodiment of the invention in which the lens receptacle itself has a closeable well for containing a tinted contact lens immersed in a fluid.
Figure 6:
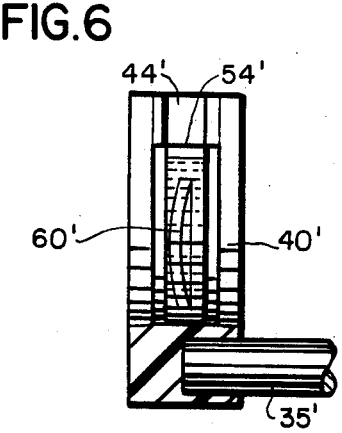
FIG. 6 is a side elevational sectional view of the lens receptacle of FIG. 5, showing a soft tinted contact lens immersed in the fluid.

The embodiment of the invention shown in FIGS. 5 and 6 is substantially the same as that of FIGS. 1-4, with corresponding parts tagged by the same reference number but with a prime designation added, except that the opening 44' in lens receptacle 40' receives the tinted soft contact lens 60' and its surrounding saline solution directly rather than in a plug-in lens holder and the opening 44' is sealed directly by flap 54' by sealing means (not shown). In this embodiment, each lens receptacle 40' may be changed by removing it by rotation from the end of elbow portion 35' and replacing it with another lens receptacle 40' having a tinted soft contact lens 60' of a different tint.

Figure 7:
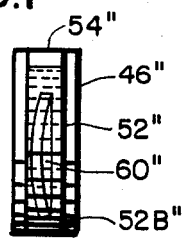
FIG. 7 is a side elevational view of an alternate embodiment of the plug-in lens holder shown in FIG. 1 with a tinted contact lens hingedly sealed in a fluid-containing well in the lens holder.
Figure 8:
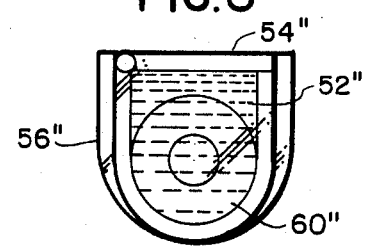
FIG. 8 is a front elevational view, partly cutaway, of the plug-in lens holder of FIG. 7.

The embodiment of the lens holder shown in FIGS. 7 and 8 is substantially the same as that shown in FIGS. 1-4, with corresponding parts tagged by the same reference number but with a double prime designation added, the only difference being that well 52" is sealed by a hinged cover 54" in place of the closure 54.

Figure 9:
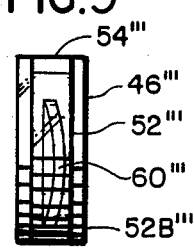
FIG. 9 is a side elevational view of the plug-in lens holder for a tinted hard contact lens, or a tinted gas permeable lens, similar to the FIG. 8 embodiment, but with no fluid contained in the opening of the lens holder.

The embodiment of the lens holder shown in FIG. 9 is substantially the same as that shown in FIGS. 1-4, with corresponding parts tagged by the same reference number but with a triple prime designation added, except that its well 52''' contains either a tinted hard contact lens 60''' or a tinted gas permeable contact lens 60''' and there is no fluid in the well 52'''.

Figure 10:
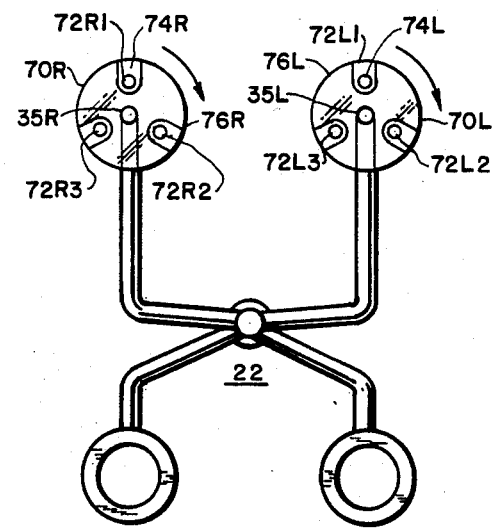
FIG. 10 is a front elevational view of still another embodiment of the invention in which the scissors support has rotating disc lens holders.

Referring to the embodiment shown in FIG. 10, the tinted contact lens fitter has a scissors type support means 22 which is the same as that of the preferred embodiment shown in FIGS. 1-4; but rotating discs 70R and 70L replace the combined lens receptacles 40 and lens holders 46 of the embodiment of the invention shown in FIGS. 1-4.

Each disc 70 has three U-shaped openings 72 spaced 120 degrees apart. Each opening 72 is adapted to receive a tinted contact lens 74. If the tinted contact lens 74 is a soft contact lens, then it is immersed in a saline solution. If the tinted contact lens 74 is a hard contact lens or a gas permeable lens, there is no fluid in the opening 72. A sealing ring 76 is cemented around the periphery of each disc 70 to contain the tinted contact lens 74 and any saline solution. As in the FIGS. 5-6 embodiment, each disc 70 may be changed by being removed from the end of elbow portion 35 and replaced by another disc 70.

In operation, each of the openings 72 contains a tinted contact lens 74 of a different color, with pairs of discs 70 having matching tints in corresponding openings 72. First, the patient, with the aid of the opthamologist or optometrist, adjusts the angle between the levers 24 so that the center of the contact lens 74 in each of the vertical top openings 72 is aligned with the centers of the patient's pupils, as similarly shown in FIG. 11. Then the resulting combined color of the tint of the contact lenses 74 and the patient's iris color is examined in a mirror (not shown). Then the patient or the fitter rotates the discs 70 together to bring to the vertical top position a different pair of contact lens 74 having a matching tint, and checks the resulting combined color, until a desired tint is determined.

Thus each disc 70 permits the trial of three different tints. And other pairs of discs 70, with contact lens 74 is still different tints, may be substituted for the attached pair of discs 70.

While FIG. 10 shows the tinted contact lenses 72-1 to 72-3 permanently inserted into wells in the rotating discs 70, the lenses 72 may be mounted in lens holders like lens holders 46 of the FIGS. 1-4 embodiment and inserted into corresponding openings like openings 44 of the FIGS. 1-4 embodiment.

While a patient preferably uses the tinted contact lens fitters 20 shown in the various embodiments with a mirror, the fitter may use a video camera to record the resulting color changes with different tinted lenses and play back the recording on a video cassette recorder in view of the patient.

Another method of viewing the resultant colors with different tinted lenses is by taking photographs with a Polaroid camera and showing the photographs to the patient.

The supporting means of each of the embodiments is preferably made from clear plastic with stainless steel as an alternative material. The lens receptacles, lens holders and discs are preferably made from crystal-clear styrene or acrilac plastic.

The diameter of tinted soft contact lenses is 15 mm and the inside width of the wall 52 (FIGS. 1-4), the opening 44' (FIGS. 5-6), well 52" (FIGS. 7-8) and the opening 72 (FIG. 10) is each slightly more than 15 mm, their height is about 18 mm and their thickness about 5 mm.

The diameter of tinted hard contact lenses is about 9 mm so that the inside width of well 52''' (FIG. 9) is slightly larger than 9 mm, its height about 10 mm and its width about 2.5 mm.

The diameter of tinted gas permeable lenses is about 9.5 to 11.5 mm so that the inside width of well 52''' (FIG. 9) is from 10 to 12 mm, its height about 12 mm and its width about 2.5 mm.

Tinted hard contact lenses and tinted gas permeable lenses may also be used with the embodiments of the invention shown in FIGS. 1-8, but with well 52, opening 44', well 52" and opening 72 correspondingly reduced in dimensions and with no fluids.

What is claimed is:

1. A tinted contact lens fitter comprising:
   (A) a first tinted contact lens holder means for holding a first tinted contact lens;
   (B) a second tinted contact lens holder means for holding a second tinted contact lens;
   (C) said first and second tinted contact lens holder means each comprising a rotatable disc having a plurality of closed wells each containing a tinted contact lens of a different tint; and
   (D) supporting means attached to said first and second tinted contact lens holder means for supporting said first and second tinted contact lens holder means laterally spaced from, and substantially in the same plane with, each other;
   (E) said supporting means including spacing means for varying the lateral spacing between said first and second tinted contact lens holder means so that the center of a first tinted contact lens held by said first tinted contact lens holder means may be substantially aligned with the center of and close to a person's pupil, and the center of a second contact lens held by said second tinted contact lens holder means may be substantially aligned with the center of and close to that person's other pupil;
   (F) whereby that person may view in a mirror the color resulting from the combination of the tint of each of said first and second tinted contact lens and the natural color of that person's adjacent iris.

2. A tinted contact lens fitter according to claim 1 wherein each of said closed wells also contains a fluid.

3. A tinted contact lens fitter comprising:
   (A) a first tinted contact lens holder means for holding a first tinted contact lens;
   (B) a second tinted contact lens holder means for holding a second tinted contact lens; and
   (C) scissors supporting means attached to said first and second tinted contact lens holder means for supporting said first and second tinted contact lens holder means laterally spaced from, and substantially in the same plane with, each other;
   (D) said scissors supporting means being operable for varying the lateral spacing between said first and second tinted contact lens holder means so that the center of a first tinted contact lens held by said first tinted contact lens holder means may be substantially aligned with the center of and close to a person's pupil, and the center of a second contact lens held by said second tinted contact lens holder means may be substantially aligned with the center of and close to that person's other pupil;
   (E) whereby that person may view in a mirror the color resulting from the combination of the tint of each of said first and second tinted contact lens and the natural color of that person's adjacent iris.

4. A tinted contact lens fitter according to claim 3 wherein said first and second tinted contact lens holder means each comprises a lens receptacle having an opening and a lens holder adapted to be mounted in the opening of said lens receptacle, said lens holder adapted to hold a tinted contact lens.

5. A tinted contact lens fitter according to claim 4 wherein said lens holder comprises a body having a well adapted to contain a fluid and a tinted contact lens.

6. A tinted contact lens fitter according to claim 5 wherein said lens holder has a closure for closing said well to prevent a fluid in said well from leaking from said well.

7. A tinted contact lens fitter according to claim 3 wherein said first and second tinted contact lens holder means each further comprises a closed well with a tinted contact lens in said well.

8. A tinted contact lens fitter according to claim 7 wherein said well also contains a fluid.

9. A tinted contact lens fitter according to claim 3 wherein said first and second tinted contact lens holder means each further comprises a rotatable disc having a plurality of closed wells each containing a tinted contact lens of a different tint.

10. A tinted contact lens fitter according to claim 9 wherein each of said closed wells also contains a fluid.

11. A tinted contact lens fitter according to claim 3 wherein said scissors supporting means comprises two levers connected at a hinge.

12. A tinted contact lens fitter according to claim 11 wherein each of said levers comprises a handle having a ring at its end on one side of said hinge and a shank having a bent elbow portion at its end on the other side of said hinge with said bent elbow portion connected to one of said tinted contact lens holder means.

13. A tinted contact lens fitter according to claim 12 wherein said first and second tinted contact lens holder means each comprises a lens receptacle having an opening and a lens holder adapted to be mounted in the opening of said lens receptacle, said lens holder adapted to hold a tinted contact lens.

14. A tinted contact lens fitter according to claim 13 wherein said lens holder comprises a body having a well adapted to contain a fluid and a tinted contact lens.

15. A tinted contact lens fitter comprising tinted contact lens holder means for holding tinted contact lenses, said tinted contact lens holder means comprising a rotatable disc having a plurality of closed wells each containing a tinted contact lens of a different tint, and supporting means attached to said tinted contact lens holder means for supporting said tinted contact lens holder means so that the center of a tinted contact lens held by said tinted contact lens holder means may be substantially aligned with the center of and close to a person's pupil, whereby that person may view in a mirror the color resulting from the combination of the tint of said tinted contact lens and the natural color of that person's adjacent iris.

16. A tinted contact lens fitter according to claim 15 wherein each of said closed wells also contains a fluid.

* * * * *